United States Patent [19]

Eibl et al.

[11] 4,276,283

[45] Jun. 30, 1981

[54] METHOD OF PREPARING AN INTRAVENOUSLY ADMINISTRABLE IMMUNE GLOBULIN PREPARATION CONTAINING ANTIBODIES AND PREPARATIONS PRODUCED ACCORDING TO THIS METHOD

[75] Inventors: Martha Eibl; Otto Schwarz; Yendra Linnau, all of Vienna, Austria

[73] Assignee: Immuno Aktiengesellschaft für chemisch-medizinische Produkte, Austria

[21] Appl. No.: 74,257

[22] Filed: Sep. 10, 1979

[30] Foreign Application Priority Data

Sep. 19, 1978 [AT] Austria ................................ 6753/78

[51] Int. Cl.³ .................... A61K 39/395; A61K 39/00
[52] U.S. Cl. .................................. 424/85; 260/112 B; 424/86; 424/87
[58] Field of Search ....................... 260/112 B; 424/85

[56] References Cited

U.S. PATENT DOCUMENTS

| | | | |
|---|---|---|---|
| 3,415,804 | 12/1968 | Polsom | 260/112 B |
| 3,763,135 | 10/1973 | Shanbrom et al. | 260/112 B |
| 4,093,606 | 6/1978 | Coval | 260/112 B |
| 4,126,605 | 11/1978 | Schneider et al. | 260/112 B |
| 4,165,370 | 8/1979 | Coval | 260/112 B |

FOREIGN PATENT DOCUMENTS

| | | |
|---|---|---|
| 329747 | 5/1976 | Austria . |
| 344883 | 8/1978 | Austria . |
| 2606118 | 8/1976 | Fed. Rep. of Germany . |
| 1372953 | 11/1974 | United Kingdom . |

*Primary Examiner*—Delbert R. Phillips
*Assistant Examiner*—Blondel Hazel
*Attorney, Agent, or Firm*—Brumbaugh, Graves, Donohue & Raymond

[57] ABSTRACT

A method of preparing an intravenously administrable immune globulin preparation containing antibodies, in which human blood plasma is fractionated and an immune-globulin-containing fraction is freed from undesired protein impurities by a single or repeated precipitation with polyethylene glycol, is characterized in that the immune-globulin-containing fraction is subjected in a first purification step prior to the polyethylene glycol precipitation to a treatment with an aqueous solution of a salt of an inorganic acid, and in that at least one of the following purification steps is carried out with polyethylene glycol in the presence of a soluble carbohydrate or a non-protein-precipitating polyol, whereupon the immune globulin freed from protein impurities is precipitated from the remaining solution by water-soluble polymers and is finished in a known manner to the pharmaceutical preparation.

11 Claims, 1 Drawing Figure

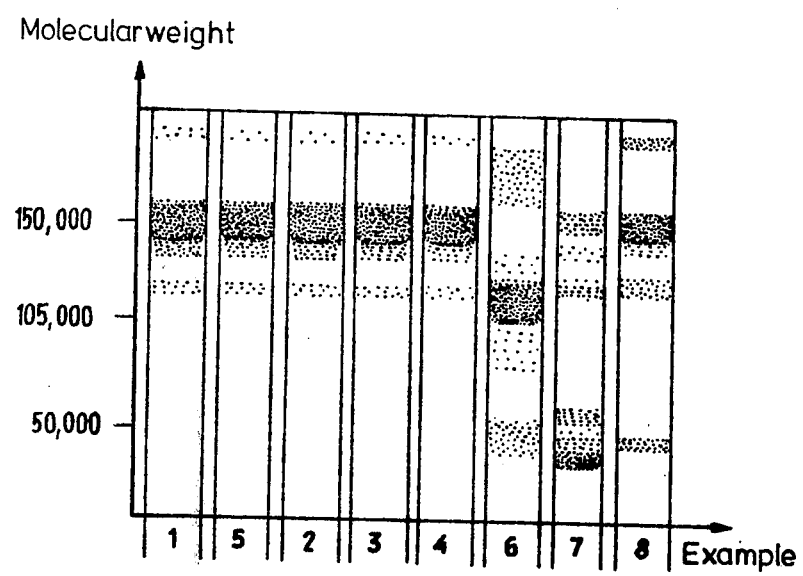

METHOD OF PREPARING AN INTRAVENOUSLY ADMINISTRABLE IMMUNE GLOBULIN PREPARATION CONTAINING ANTIBODIES AND PREPARATIONS PRODUCED ACCORDING TO THIS METHOD

The invention relates to a method of preparing an intravenously administrable immune globulin preparation containing antibodies, wherein human blood plasma is fractionated and a fraction containing immune globulin is freed from undesired protein impurities by a single or repeated precipitation with polyethylene glycol, as well as to preparations prepared according to this method.

After having overcome an infection, the human organism generally will be protected against a second infection with the same germ. Such a protection can be achieved also by inoculation; it is based on the development of cellular and humoral immunity. While the cellular immunity is borne by lymphocytes, the responsibility for the humoral immunity lies with various specific antibodies. Antibodies are high-molecular proteins having globulin character which occur in the blood. The full development of the humoral immunity may extend over the first two life decades, being weakest particularly between the sixth and twenty-fourth months of life. It has been known for some time (1952 Bruton) that certain patients may lack antibodies (antibody deficiency syndrome), it being mostly a disease with family incidence. Such patients suffer from different, frequently recurring infections, which sometimes assume life-endangering dimensions. Similar antibody deficiency conditions cannot only occur genetically, but can also be acquired, mostly occurring as a selective or partial antibody deficiency syndrome (ADS).

Since such patients are not able to produce the antibodies lacking, these latter have to be supplied to them to sufficient extents, for the treatment or prevention of infections. The effect of such a substitution is limited in time, the duration of efficacy depending on the biological half-life values of the antibodies supplied. The antibodies produced in the organism have a biological half-life of three to four weeks.

It has been known to prepare immune globulin containing antibodies by e.g. fractionating human blood plasma according to the socalled Cohn-method (J. L. Oncley, M. Melin, D. A. Richert, J. W. Cameron and P. M. Gross, Jr. "The Separation of the Antibodies, Isoagglutinins, Prothrombin, Plasminogen and $\beta_1$-Lipoprotein into Subfractions of Human Plasma", J.Am.-Chem.Soc., volume 71, page 541 (1949),) by alcohol precipitation. These preparations are suitable for intramuscular application, yet they are not suited for intravenous application, for by-products will form during the production process which have harmful properties. If injected intravenously, they sometimes will lead, already during the injection, to extensive incompatibility reactions of, however, short duration, e.g. a decrease in blood pressure, which may bring about life-endangering conditions. In order to obtain intravenously injectable compatible immune globulins, immune globulins hitherto have been enzymatically degraded or chemically modified. By this, the therapeutical effect and the biologic quality of the immune globulin preparations were, however, inversely affected. Not only were the immune globulin molecules reduced by the enzymatic treatment, thus decreasing the quality of the antibodies, but the emerging cleavage products also competitively inhibit the desired antigen/antibody reaction and/or bonding of the antigen/antibody complexes to Fc-receptors. Another disadvantage of such modified immune globulins is a shortened biological half-life.

A further disadvantage with chemically modified immune globulins is the occurrence of new antigenic specificities, which eventually may lead to additional incompatibility reactions, when repeatedly administered.

A further method belonging to the prior art (German Offenlegungsschrift No. 26 06 118), according to which the preparation of gammaglobulin that is suited for intravenous injection has been aimed at, comprises a stepwise purification of a plasma protein suspension with polyethylene glycol and a complete precipitation with polyethylene glycol. The polyethylene glycol purification steps are carried out with as low an ionic concentration as possible, which has been considered essential for preventing a denaturation of the proteins. However, as was found out, the realization of the fractionation with an extremely low ionic concentration is consuming and the products prepared are not free from incompatibility signs.

Finally, a further method belongs to the prior art (Austrian Pat. No. 344,883), according to which gammaglobulin preparations that are destined for intravenous application are gained from a plasma fraction after precipitation of the anticomplementary gammaglobulin portion with PEG (polyethylene glycol) in the presence of hydroxyethyl starch; it has however proved that such a purification is not yet sufficient for intravenously applying the finished preparation without side effects.

The invention aims at avoiding the disadvantages described and has as its object to provide an intravenously administrable immune globulin preparation which has been neither enzymatically degraded nor chemically modified and which can be applied intravenously in high doses without side effects.

This object is achieved according to the invention with a method of the initially defined kind in that the immune-globulin-containing fraction, in a first purification step prior to the polyethylene glycol precipitation, is subjected to a treatment with an aqueous solution of a salt of a polyvalent inorganic acid, in particular of ammonium sulfate, and in that at least one of the subsequent purification steps with polyethylene glycol is carried out in the presence of a soluble carbohydrate or a non-protein-precipitating polyol, i.e. a polyol having at least three hydroxyl groups, whereupon the immune globulin freed from protein impurities is precipitated from the remaining solution by water-soluble polymers and is then finished to the pharmaceutical preparation in a known manner.

Suitably, the immune-globulin-containing fraction is gained from human blood plasma according to the known Cohn-method or a modified Cohn-method by precipitation with ethanol, and the ethanol contained in the fraction is removed, i.e. preferably by dialysis.

According to a preferred embodiment of the process of the invention, three purification steps are applied, wherein, in detail, it is proceeded in a manner that in a first purification step the immune-globulin-containing fraction is subjected to a treatment with an ammonium sulfate (AMS) solution having a content of 145 to 208 g/l (25 to 35% AMS-saturation) and a pH of 5.9 to 6.5; the precipitate is separated and rejected, and in a subsequent precipitation step a precipitate containing immune globulin is precipitated from the remaining solution by treatment with an ammonium sulfate solution having a content of 268 to 289 g/l (44 to 47% AMS-saturation) at a pH of 8.0; the precipitate is recovered, dissolved in water and the ammonium sulfate is removed from the solution, preferably by dialysis; that afterwards this remaining immune-globulin-containing solution in a second purification step is subjected to a treatment with polyethylene glycol at a pH of 5.8 to 6.4 in the presence of a saccharide, polysaccharide or polysaccharide hydrolysate and with an ionic strength of at least 0.15; the precipitate formed is separated and rejected, and the remaining solution in a third purification step is subjected to a further treatment with polyethylene glycol at a pH of 6.4 to 7.0, whereupon the precipitate formed anew is separated and rejected, and the immune globulin now contained in the remaining solution without harmful impurities is precipitated at a pH of 7.0 to 7.5 by a polymeric precipitation agent, and finished to the pharmaceutical preparation.

With this combination of measures, it is possible to use as a precipitating agent in the second purification step, polyethylene glycol having a molecular weight of 2,000 to 6,000 in an amount of 60 to 90 g/l, at a temperature of 0° to 40° C. Also in the third purification step, polyethylene glycol having a molecular weight of 2,000 to 6,000 can be used as a precipitating agent, i.e. suitably to an amount of 70 to 100 g/l, also at a temperature of from 0° to 40° C.

Among the soluble carbohydrates and polyols, it was particularly saccharides that proved suitable, i.e. monosaccharides, such as glucose, fructose, mannose, galactose, or disaccharides, such as saccharose, lactose, maltose, or oligo- or poly-saccharides, in an amount of 1 to 35% by weight, preferably 5 to 20% by weight, based on the solution. As soon as the purification of the immune globulins has been effected in the manner described, these can be recovered from the solution, i.e. by precipitation with water-soluble polymers. From these, copolymers of ethylene oxide and polyoxypropylene (trade name of BASF "PLURONIC"), and dextrane, polyvinyl alcohol, polyvinyl pyrrolidone and the like have proved successful. It is also possible to use polyethylene glycol as the precipitating agent for the pure immune globulin by increasing the concentration of the polyethylene glycol in the remaining solution to more than 150 g/l. The immune globulin precipitated is then processed into the pharmaceutical preparation, known measures being applicable.

Advantageously, the completion of the purified immune globulin into the pharmaceutical preparation is effected by dissolution in pyrogen-free water, further dialysis, ultrafiltration or gel filtration, adjustment of the immune globulin concentration to 5 to 200 g/l, preferably 50 to 160 g/l, and regulation of the ionic strength by means of NaCl to 0.005 to 0.3, preferably 0.1 to 0.2.

The plasma proteins contained in the end product, at least by 80%, are formed of native immune globulins having a sedimentation constant S of 7.0 and a biological half-life of 21 to 28 days. The anticomplementary activity of the product corresponds to a value according to which at least 35 mg of protein are necessary for the neutralization of a unit $C'H_{50}$. Furthermore, the preparations produced according to the invention are characterized in that they contain less than 5% of protein components having a molecular weight of more than 160,000.

The process according to the invention will now be explained in more detail by the following examples.

EXAMPLE 1

Human blood plasma is adjusted to a pH of 7.0 to 7.2 and maintained at a temperature of −2° C. 8% by weight of ethanol are added to the solution, a precipitate substantially containing fibrinogen precipitating. After separation of this precipitate, the ethanol concentration is increased to 25% by weight, and the temperature is lowered to −6° C. The precipitating precipitate, which essentially consists of raw immune globulin, is extracted in a phosphate acetate buffer and mixed with 12% by weight of ethanol at a pH of 5.3 at −2° C. The precipitate (containing alpha- and beta-globulin) is rejected and the ethanol concentration of the supernatent is increased to 25% by weight at a pH of 7.2 and a temperature of −10° C., immune globulin thus being precipitated. The collected paste-like immune globulin fraction thus prepared is further treated according to the invention in the following manner:

1 kg of the immune globulin paste is dissolved on stirring in 2 l of a 0.9% NaCl solution and dialyzed. Then, the protein concentration is adjusted to 20 g/l as well as to an ionic strength of 0.15, and 176 g/l of ammonium sulfate are added at a pH of 6.25 (first purification step), whereupon the precipitate formed containing undesired impurities is rejected and to the supernatent further ammonium sulfate is added to reach a concentration of 275 g/l and the pH is adjusted to 7.2. The precipitating immune-globulin-containing precipitate is dissolved in water and subjected to a dialysis against tap water. Then 80 g/l of polyethylene glycol are added to the solution in the presence of 150 g of glucose/l at a pH of 6.0 and an ionic strength of 0.15 (second purification step). The precipitate is rejected and the polyethylene glycol concentration is increased to 95 g/l at a pH of 6.5 to 6.6. The precipitate precipitating anew is rejected (third purification step).

Now, the content of the solution of polyethylene glycol is increased to 180 g/l at a pH of 7.2, the impurity-free immune globulin thus being precipitated. The product is centrifuged, and the polyethylene glycol still present is removed by being washed five times.

EXAMPLE 2

1 kg of immune globulin paste is gained and treated in the same manner as described in Example 1, but in the second purification step fructose in an amount of 150 g/l is added instead of glucose.

EXAMPLE 3

1 kg of immune globulin paste is gained and treated in the same manner as described in Example 1, but in the second purification step saccharose in an amount of 150 g/l is added instead of glucose.

EXAMPLE 4

0.5 kg of immune globulin paste, which was gained from human blood plasma in the same manner as described in Example 1, is dissolved in 6 l of a 0.9% NaCl solution on stirring, and ethanol is removed from the solution by ultrafiltration. The protein concentration of the remaining solution is adjusted to 20 g/l and the ionic strength is adjusted to 0.15, whereupon 119.5 g/l of disodium hydrogen phosphate are added at a pH of 6.7 (purification step). The precipitating precipitate is rejected and the supernatant is adjusted to a pH of 7.2 by means of sodium hydroxide, a further precipitate forming which is again rejected (purification step). Then 275 g/l of ammonium sulfate are added to the solution. The precipitating immune-globulin-containing precipitate is dissolved in water and dialyzed for removal of the inorganic salts. To the solution, 87.5 g/l of polyethylene glycol and 150 g/l of glucose are added and the pH is adjusted to 6.0. The precipitate is rejected (purification step), the pH of the remaining solution is increased to 6.6 and the concentration of the solution is increased to 95 g of polyethylene glycol/l by further addition of polyethylene glycol. The newly precipitating precipitate is rejected (purification step). Now, the content of the solution of polyethylene glycol is increased to 150 g/l at a pH of 7.2, the impurity-free immune globulin thus being precipitated. The product is centrifuged as in Example 1, and the polyethylene glycol present is removed by washing.

EXAMPLE 5

1 kg of immune globulin is gained and treated in the same manner as described in Example 1, however the final precipitation of the impurity-free immune globulin is effected by the addition of 38 g/l of Pluronic F 68 (a copolymer of ethylene oxide with polyoxy propylene), a pH of also 7.2 being observed.

In the following Table I, the anticomplementary activity of the immune globulin prepared according to Examples 1 to 5 is indicated, the values being determined after E. A. Kabat and M. M. Mayer "Experimental Immunochemistry" (Thomas, Springfield 1961) and Public Health Monograph No. 74: Standardized Diagnostic Complement Fixation Method and Adaptation to Microtest (Washington, 1965).

TABLE I

| Immune globulin prepared according to | Anticomplementary activity |
|---|---|
| Example 1 | 96 mg |
| Example 2 | 95 mg |
| Example 3 | 101 mg |
| Example 4 | 35 mg |
| Example 5 | 104 mg |

The preparations prepared according to Examples 1 to 5 to a proportion of more than 80% contained the 7-S-component specified in Table II. The determination was carried out in an analytic ultra-centrifuge, according to the Europte,uml/a/ chen Arzneibuch, Vol. II, Deutscher Apothekar Verlag, Stuttgart 1975, a one-percent solution (v/v) in a phosphate buffer solution of pH 6.0 to 8.0 and an ionic strength of at least 0.2 being subjected to determination.

TABLE II

| Immune globulin prepared according to | 7-S-Components |
|---|---|
| Example 1 | 95.5% |
| Example 2 | 95.5% |
| Example 3 | 98.4% |
| Example 4 | 88.0% |
| Example 5 | 98.2% |

In a further determination, the immune globulins obtained according to Examples 1 to 5 were investigated according to the sodium-dodecyl-sulfate-polyacryloamidegel-electrophoresis [SDS-PAGE, K. Weber and M. Osborn, J.Biol.Chem. 244, 4406 (1969)], a division according to their molecular weights, of the proteins obtained being reached. With the immune globulins obtained according to the invention by Examples 1 to 5 (Samples 1 to 5), the broad bands illustrated in the accompanying diagram forming at molecular weights of 150,000.

Compared to this, sample 6 is a preparation enzymatically degraded with pepsin, and sample 7 is a preparation enzymatically degraded with plasmin, the broad bands lying at lower molecular weights of 105,000 and 50,000, respectively. Sample 8 shows the molecular-weight distribution in a chemically altered preparation, wherein considerably high molecular portions of above 160,000 are present and also portions are present at lower molecular weights of about 50,000.

The preparations produced according to the invention were compared in terms of their blood-pressure influencing effect with a known blood-pressure active preparation produced according to the Cohn-method. The comparative tests were carried out in anesthetized dogs. The vena jugularis externa of the dogs was dissected at the lower edge of the mandible and catheters were introduced into both vein branches. Moreover, the carotid artery was dissected free and a catheter was bound in. The blood pressure was electromanometrically measured via the arterial catheter; the narcotic agent and the immune globulin preparations to be compared were introduced via the two other catheters on keeping the injection volume constant. The blood pressure values were controlled through 60 minutes after supplying the test substances, wherein the respective systolic and diastolic blood pressure values were determined, an average value having been recorded. The doses administered each amounted to 150 mg/kg. The results are illustrated in the following table:

| | Blood Pressure in mm/Hg (average values) | | | | | |
|---|---|---|---|---|---|---|
| | at onset | after 5 min | after 10 min | after 20 min | after 30 min | after 60 min |
| Preparation prepared according to invention | 100 | 94 | 100 | 100 | 98 | 98 |
| Known preparation | 100 | 43 | 58 | 58 | 70 | 90 |

What we claim is:

1. A method of preparing an immune globulin preparation suitable for intravenous administration from an immune-globulin-containing fraction of blood plasma, which comprises
    (a) purifying the immune-globulin-containing fraction, by treating it with an aqueous solution of a polyvalent salt selected from the group consisting of ammonium sulfate and an alkali phosphate, thereby obtaining a precipitate, which is separated from the aqueous solution and discarded and an immune-globulin-containing supernatant, and
    (b) treating the supernatant from step (a) with an aqueous solution of a polyvalent salt selected from the group consisting of ammonium sulfate and an alkali phosphate, the salt solution having a higher concentration than the solution employed in step (a) thereby obtaining an immune-globulin-containing precipitate which is retained and a supernatent, which is discarded, and (c) dissolving the precipitate containing immune globulin and the polyvalent salt in water and removing the polyvalent salt from the solution, and (d) further purifying the solution from step (c) with polyethylene glycol in the presence of a saccharide selected from the group consisting of monosaccharide and disaccharide at an ionic strength of at least 0.15, thereby obtaining a supernatant containing immune globulin and a precipitate, which is separated and discarded, and (e) further purifying the supernatant from step (d) by an additional treatment with polyethylene glycol, having a higher concentration than in step (d) thereby obtaining an immune-globulin-containing solution free from noxious impurities and a precipitate, which is separated and discarded, and (f) treating the solution from step (e) with a water-soluble polymer selected from the group consisting of copolymers of ethylene oxide and polyoxypropylene (Pluronic), dextran, polyvinyl alcohol, polyvinyl pyrrolidone and polyethylene glycol, thereby obtaining an immune globulin precipitate, which can be formulated into a pharmaceutical preparation which can be administered intravenously.

2. A method of preparing an immune globulin preparation suitable for intravenous administration from an immune-globulin-containing fraction of human blood plasma, which comprises (a) purifying the immune-globulin-containing fraction, by treating it with an ammonium sulfate containing about 145 to 208 g ammonium sulfate/l at a pH of about 5.9 to 6.5, thereby obtaining a precipitate, which is separated and discarded, and an immune-globulin-containing supernatant, and (b) treating the supernatant from step (a) with an ammonium sulfate solution containing about 268 to 289 g ammonium sulfate/l at a pH of about 7.2 to 8.0, thereby obtaining an immune-globulin-containing precipitate which is retained and a supernatant, which is discarded, and (c) dissolving the precipitate containing immuneglobulin and the ammonium sulfate in water, and removing the ammonium sulfate from the solution, and (d) further purifying the solution from step (c) with polyethylene glycol at a pH of 5.8 to 6.4 in the presence of a monosaccharide or disaccharide and at an ionic strength of at least 0.15, thereby obtaining a supernatant containing immune globulin and a precipitate, which is separated and discarded, and (e) further purifying the supernatant from step (d) by an additional treatment with polyethylene glycol at a pH of about 6.4 to 7.0, thereby obtaining an immune-globulin-containing solution free from noxious impurities and a precipitate, which is separated and discarded, and (f) treating the solution from step (e) with a copolymer of ethylene oxide and polyoxypropylene (Pluronic) at a pH of about 7.0 to 7.5, thereby obtaining an immune globulin precipitate, which can be formulated into a pharmaceutical preparation which can be administered intravenously.

3. A method as set forth in claim 2, wherein the ammonium sulfate is removed by dialysis.

4. A method of preparing an immune globulin preparation suitable for intravenous administration from an immune-globulin-containing fraction of human blood plasma, which comprises (a) purifying the immune-globulin-containing fraction, treating it with an ammonium sulfate solution containing about 145 to 208 g ammonium sulfate/l at a pH of about 5.9 to 6.5, thereby obtaining a precipitate, which is separated and discarded, and an immune-globulin-containing supernatant, and (b) treating the supernatant from step (a) with an ammonium sulfate solution containing about 268 to 289 g ammonium sulfate/l at a pH of about 7.2 to 8.0, thereby obtaining an immune-globulin-containing precipitate which is retained and a supernatant, which is discarded, and (c) dissolving the precipitate containing immune globulin and the ammonium sulfate in water and removing the ammonium sulfate from the solution, and (d) further purifying the solution from step (c) with polyethylene glycol having a molecular weight of about 2000 to 6000 at a pH of about 5.8 to 6.4 and in an amount of 60 to 90 g/l at a temperature of 0° to 40° C. in the presence of a monosaccharide or disaccharid and at an ionic strength of at least 0.15, thereby obtaining a supernatant containing immune globulin and a precipitate, which is separated and discarded, and (e) further purifying the supernatant by an additional treatment with polyethylene glycol having a molecular weight of about 2000 to 6000 at a pH of 6.4 to 7.0 and in an amount of 70 to 100 g/l at a temperature of 0° to 40° C., thereby obtaining an immune-globulin-containing solution free from noxious impurities and a precipitate, which is separated and discarded, and (f) treating the solution from step (e) with a polyethylene glycol at a pH of 7.0 to 7.5 in an amount increased to 180 g/l, thereby obtaining an immune globulin precipitate, which can be formulated into a pharmaceutical preparation which can be administered intravenously.

5. A method as set forth in claim 2, wherein said monosaccharide or disaccharide is used in an amount of 1 to 35% by weight.

6. A method as set forth in claim 5, wherein said monosaccharide is selected from the group consisting of glucose, fructose, mannose and galactose.

7. A method as set forth in claim 5, wherein said disaccharide is selected from the group consisting of saccharose, lactose and maltose.

8. A method as set forth in claim 5, wherein said saccharide is used in amount of 5 to 20% by weight.

9. A method as set forth in claim 1, wherein the immune globulin preparation is formulated from the immune globulin precipate from step (f) by dissolving the precipitate thereof in pyrogen-free water, dialyzing the solution, subjecting it to ultrafiltration or gel filtration, and adjusting the immune globulin concentration to about 5 to 200 g/l and adjusting the ionic strength of the solution by means of NaCl to 0.005 to 0.3.

10. A method as set forth in claim 9, wherein the immune globulin concentration is adjusted to 50 to 160 g/l.

11. A method as set forth in claim 9, wherein the ionic strength is adjusted to 0.1 to 0.2.

* * * * *

UNITED STATES PATENT AND TRADEMARK OFFICE
CERTIFICATE OF CORRECTION

PATENT NO. : 4,276,283
DATED : June 30, 1981
INVENTOR(S) : Eibl et al.

It is certified that error appears in the above—identified patent and that said Letters Patent is hereby corrected as shown below:

Col. 4, line 28, "supernatent" should read --supernatant--.

Col. 5, line 48, "Europte,uml/a/ chen" should read --Europäischen--; line 49, "Apothekar" should read --Apotheker--.

Col. 6, line 37, "(average)" should read --(average--; line 67, "supernatent" should read --supernatant--.

Col. 7, lines 41 & 42, "immuneg-lobulin" should read --immune-globulin--.

Signed and Sealed this

Fifteenth Day of September 1981

[SEAL]

Attest:

GERALD J. MOSSINGHOFF

Attesting Officer

Commissioner of Patents and Trademarks